US009176111B2

(12) United States Patent
Chalmers et al.

(10) Patent No.: US 9,176,111 B2
(45) Date of Patent: Nov. 3, 2015

(54) BIOLOGICAL CELL SEPARATOR AND DISPOSABLE KIT (71) Applicant: Ohio State Innovation Foundation, Columbus, OH (US)

(72) Inventors: Jeffrey J. Chalmers, Columbus, OH (US); Maciej Zborowski, Bay Village, OH (US); Lee Moore, Sagamore Hills, OH (US)

(73) Assignees: Ohio State Innovation Foundation, Columbus, OH (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/663,309

(22) Filed: Mar. 19, 2015

(65) Prior Publication Data

US 2015/0252404 A1 Sep. 10, 2015

Related U.S. Application Data (63) Continuation of application No. 13/758,695, filed on Feb. 4, 2013, now abandoned, which is a continuation of application No. 13/579,707, filed as application No. PCT/US2011/025245 on Feb. 17, 2011, now abandoned.

(60) Provisional application No. 61/305,380, filed on Feb. 17, 2010.

(51) Int. Cl.
*G01N 33/487* (2006.01)
(52) U.S. Cl.
CPC .................................... *G01N 33/487* (2013.01)
(58) Field of Classification Search
CPC .................................................. G01N 33/487
See application file for complete search history.

(56) References Cited

U.S. PATENT DOCUMENTS 5,779,892 A * 7/1998 Miltenyi et al. ................ 210/222
6,129,848 A 10/2000 Chen et al.
(Continued)

FOREIGN PATENT DOCUMENTS

DE 102004040785 A1 3/2006
WO 2004078316 A 9/2004
WO 2008133726 A2 11/2008

OTHER PUBLICATIONS

International Search Report and Written Opinion of the International Searching Authority in related application No. PCT/US2011/025245, issued Apr. 28, 2011.

(Continued)

*Primary Examiner* — Sally Merkling
(74) *Attorney, Agent, or Firm* — Meunier Carlin & Curfman LLC (57) ABSTRACT A disposable kit for use in directing fluid through a biological cell separator device (10). The kit generally includes a separator tube (22), a buffer fluid container (34), cell sample container (32), separated cell container (60), and flushing fluid container (62), as well as various conduits (36, 38, 42, 50, 50a, 50b) for connecting the containers (32, 34, 60, 62) and separator tube (22) in fluid communication together. A cell separator system is provided including a separator tube (22), magnet (20), pump (120) and a motorized drive unit (96). The motorized drive unit (96) is operatively connected to the magnet (20) to allow the magnet (20) to be moved a sufficient distance away from the separator tube (22) so as to allow cells adhered to the inside surface thereof to be flushed out of the tube (22).

7 Claims, 8 Drawing Sheets

(56) References Cited

U.S. PATENT DOCUMENTS

| | | |
|---|---|---|
| 6,346,196 B1 | 2/2002 | Bose |
| 7,118,852 B2 | 10/2006 | Purdum |
| 2005/0155921 A1 | 7/2005 | Siddiqi |
| 2008/0014181 A1 * | 1/2008 | Ariff et al. .................. 424/93.7 |

OTHER PUBLICATIONS

International Search Report in related application No. PCT/US2007/084685, published Jan. 20, 2011.

* cited by examiner

BIOLOGICAL CELL SEPARATOR AND DISPOSABLE KIT

CROSS REFERENCE TO RELATED APPLICATIONS

This application is a continuation application of U.S. patent application Ser. No. 13/758,695 filed Feb. 4, 2013, which is a continuation application of U.S. patent application Ser. No. 13/579,707, which is a 371 National Phase Application of PCT/US2011/025245, filed Feb. 17, 2011, which claims the benefit of priority of U.S. Provisional Patent Application Ser. No. 61/305,380, filed Feb. 17, 2010, the disclosures of which are fully incorporated by reference herein.

SUMMARY

In one embodiment, a disposable kit is provided for directing a fluid sample of biological cells through a separator device and collecting separated cells from the sample. The kit includes a sample receiving container including an inlet and an outlet, the inlet coupled with an inlet conduit for receiving a buffer fluid and the outlet coupled with an outlet conduit. A separator tube is provided in the kit, and includes an inlet end and an outlet end The inlet end is coupled with the outlet conduit from the sample receiving container. The separator tube has a flow channel, which may be annular in cross sectional shape, for receiving a flow of the buffer fluid and sample. A separated cell container is further provided and includes an inlet port and a vacuum port. A separated cell conduit is coupled for fluid communication between the outlet end of the separator tube and the inlet port of the separated cell container. A flushing fluid container is also provided and includes an inlet port and a vacuum port. A flushing conduit is coupled for fluid communication between the outlet end of the separator tube and the inlet port of the flushing fluid container.

The kit can further include a buffer fluid container coupled with the inlet conduit to the sample receiving container. At least a portion of the outlet conduit from the sample receiving container may comprise a flexible tubing for receipt within a first pinch valve. At least a portion of the separated cell conduit may comprise a flexible tubing for receipt within a second pinch valve. At least a portion of the flushing conduit may comprise a flexible tubing for receipt within a third pinch valve. A venting conduit may be connected for fluid communication with the flushing fluid container. A first pump conduit is coupled with the vacuum port of the separated cell container, and a second pump conduit is coupled with the vacuum port of the flushing fluid container.

In another embodiment, a device is provided that separates a first group of biological cells from a mixture of at least first and second groups of cells in a suspending fluid. The device comprises a flow channel having a length, a magnet, a pump, and a motorized drive unit. The magnet is mounted along at least a portion of the length of the flow channel, such that a magnetic field is provided through at least a selected portion of the flow channel. The pump is operatively connected to the flow channel and is configured to direct the suspending fluid through the flow channel. The motorized drive unit is operatively coupled to the magnet and is adapted to move the magnet along the length of the flow channel to lessen the effect of the magnetic field on the selected portion of the flow channel. Preferably, the motorized drive unit is configured to move the magnet away from the flow channel by a distance sufficient to allow flushing of cells from an interior wall of the flow channel.

Various additional features of the invention and the illustrative embodiments will become more apparent from a review of the following detailed description of the illustrative embodiments.

DETAILED DESCRIPTION

Figure 1:
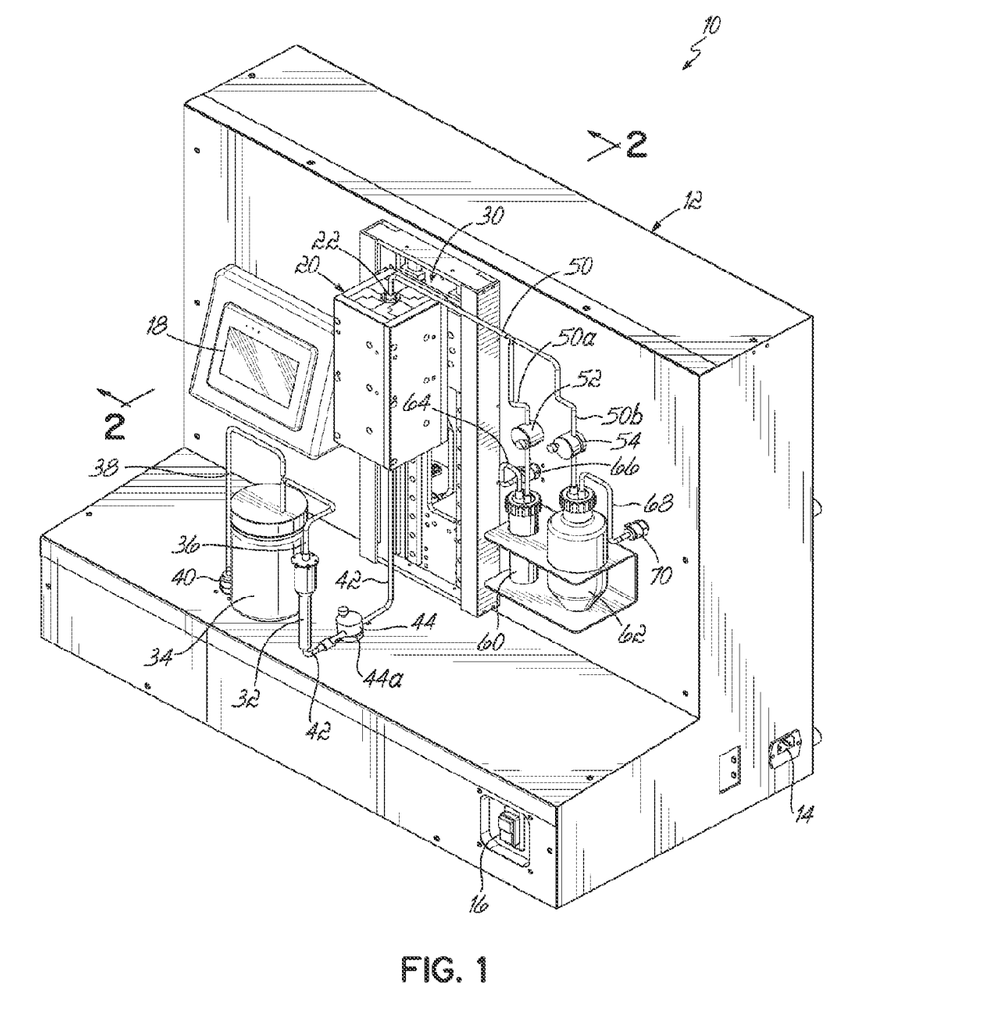
FIG. 1 is a perspective view of a cell separator device constructed according to an illustrative embodiment.
Figure 2:
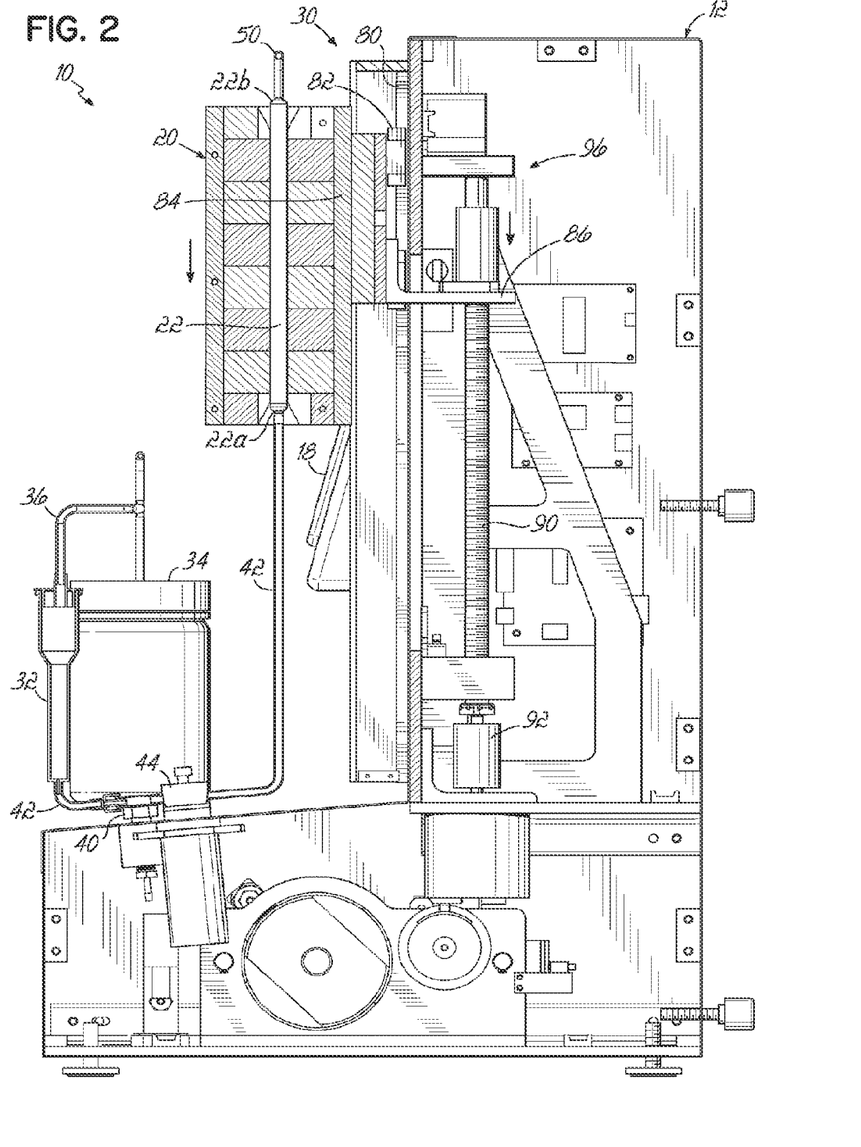
FIG. 2 is a cross sectional view of the device shown in FIG. 1, taken along line 2-2 thereof.
Figure 3:
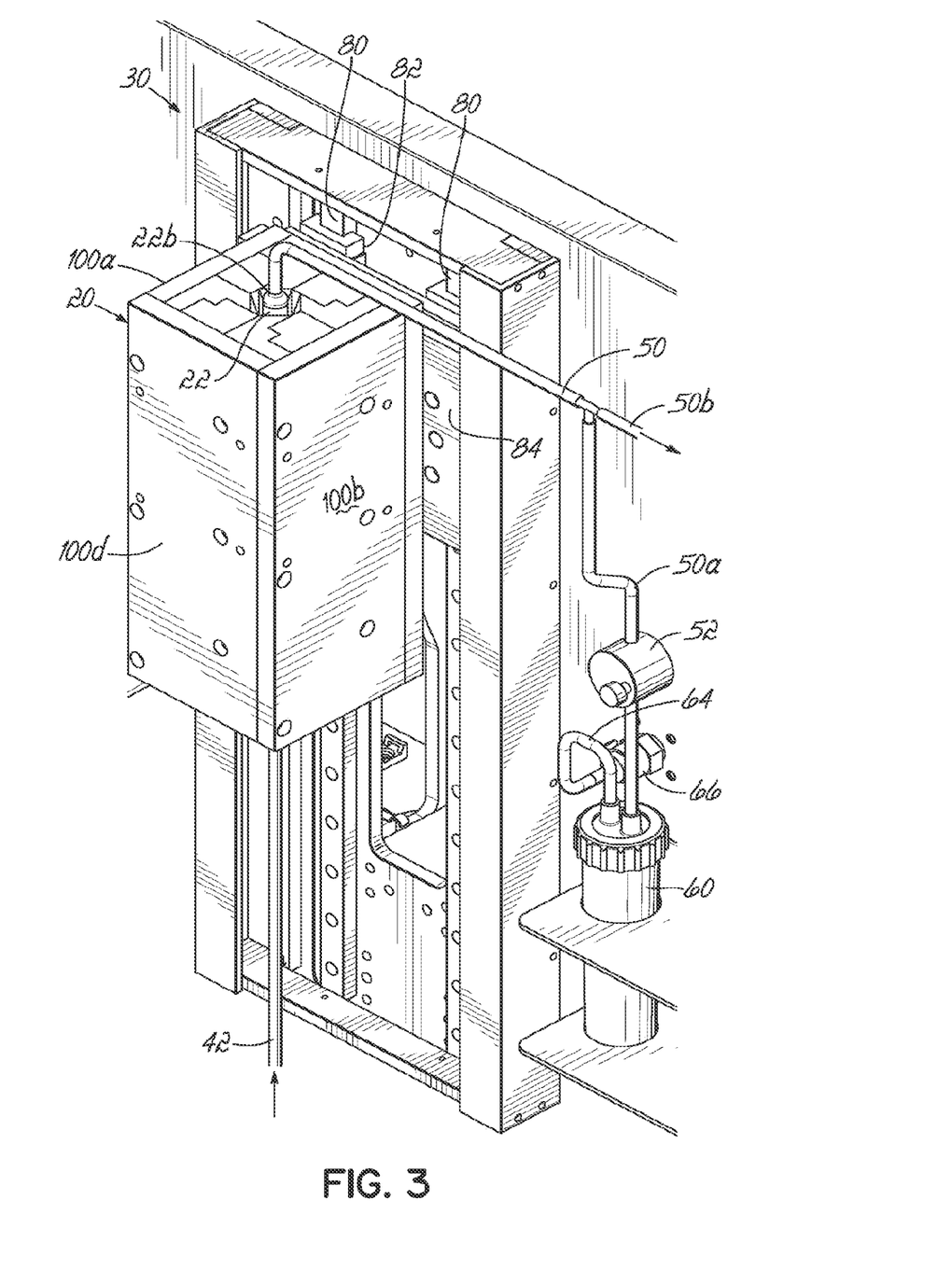
FIG. 3 is an enlarged perspective view of a portion of the device shown in FIG. 1, including the magnet and separated cell container.
Figure 4:
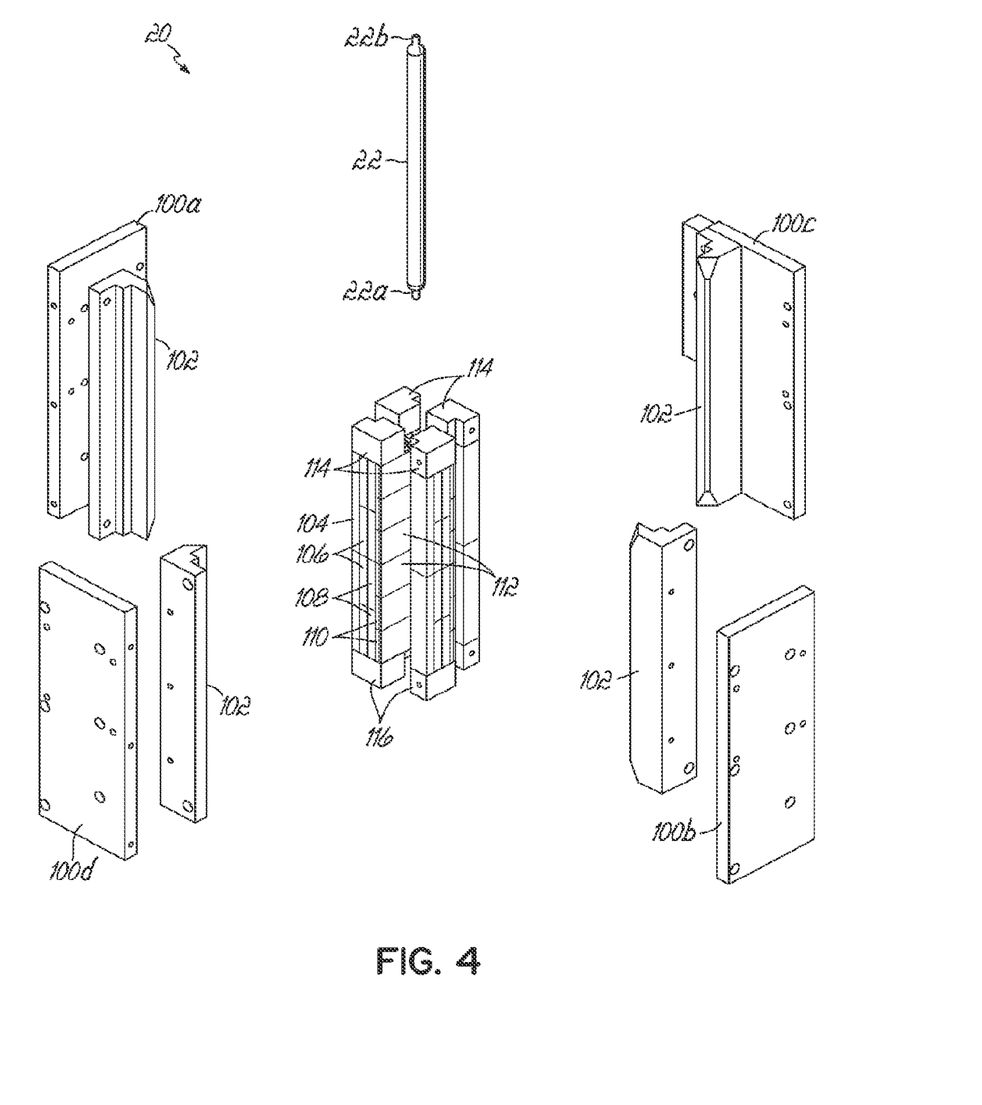
FIG. 4 is an exploded perspective view of the magnet and separator tube associated with the device of FIG. 1.
Figure 5:
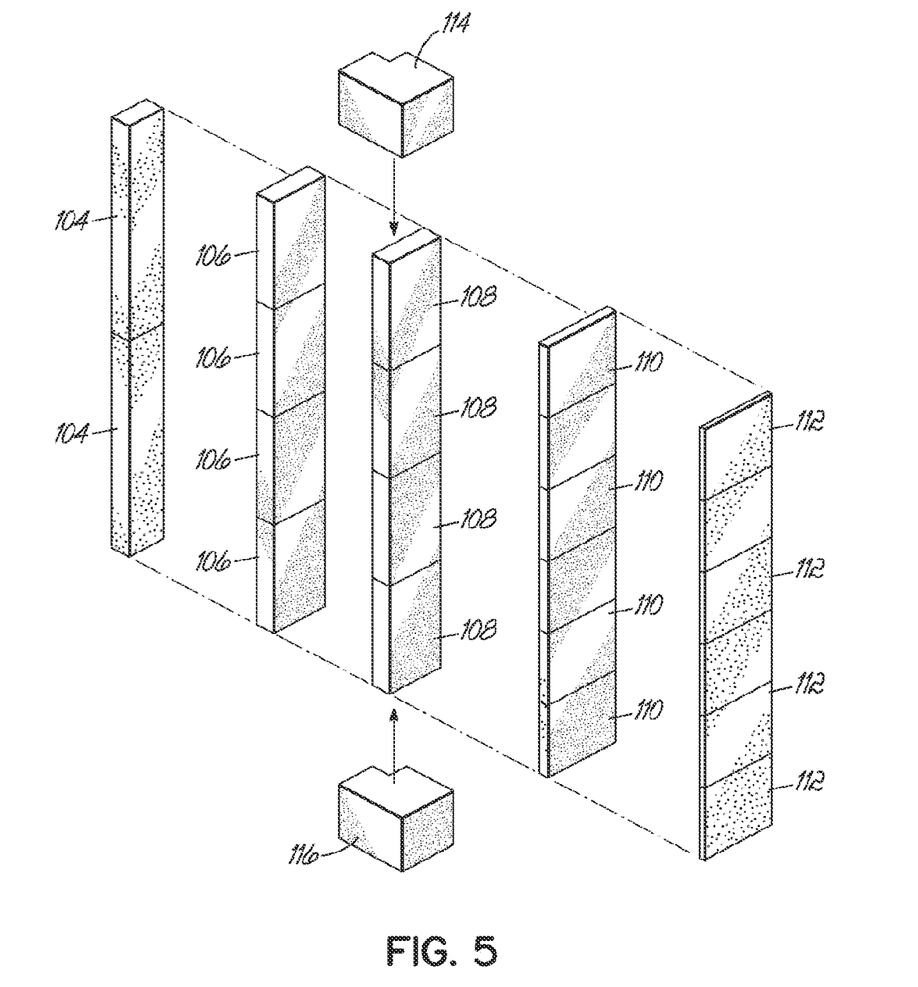
FIG. 5 is an exploded perspective view of a portion of the magnet.
Figure 6:
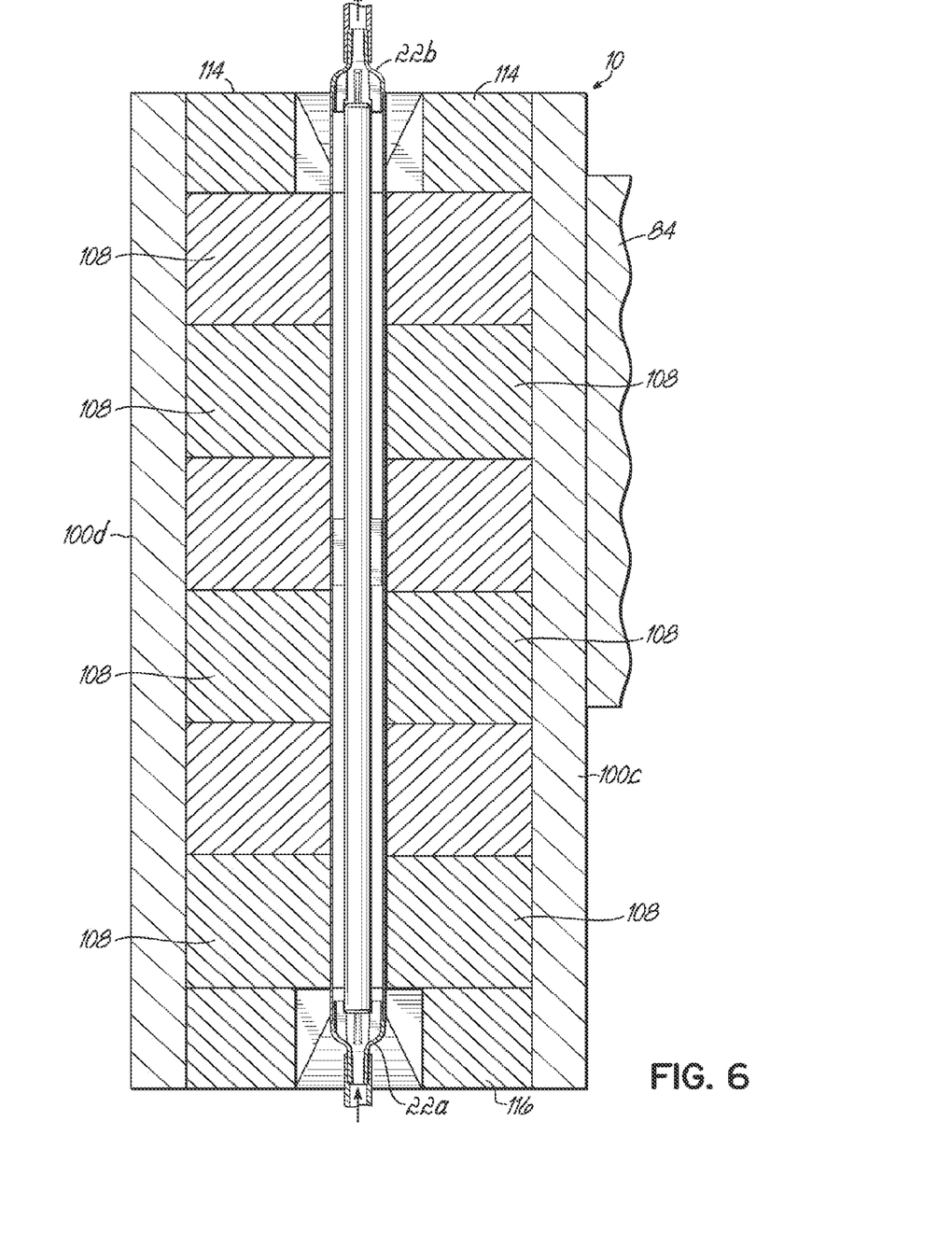
FIG. 6 is a cross sectional view of the magnet and separator tube taken in a plane along the longitudinal axis thereof.

Referring first to FIGS. 1-3, a device 10 is shown and includes a housing or support structure 12. An electrical power plug 14 is provided for receiving a power cord to supply electric current to the various electric components associated with the device 10. A main on/off power switch 16 is provided, as well as a control panel 18 for allowing the user to operate the device 10. A magnet 20 receives a separator tube 22 for purposes to be discussed further below. The magnet 20 is supported by a support or mounting structure 30 for vertical movement, as also discussed below.

Figure 8:
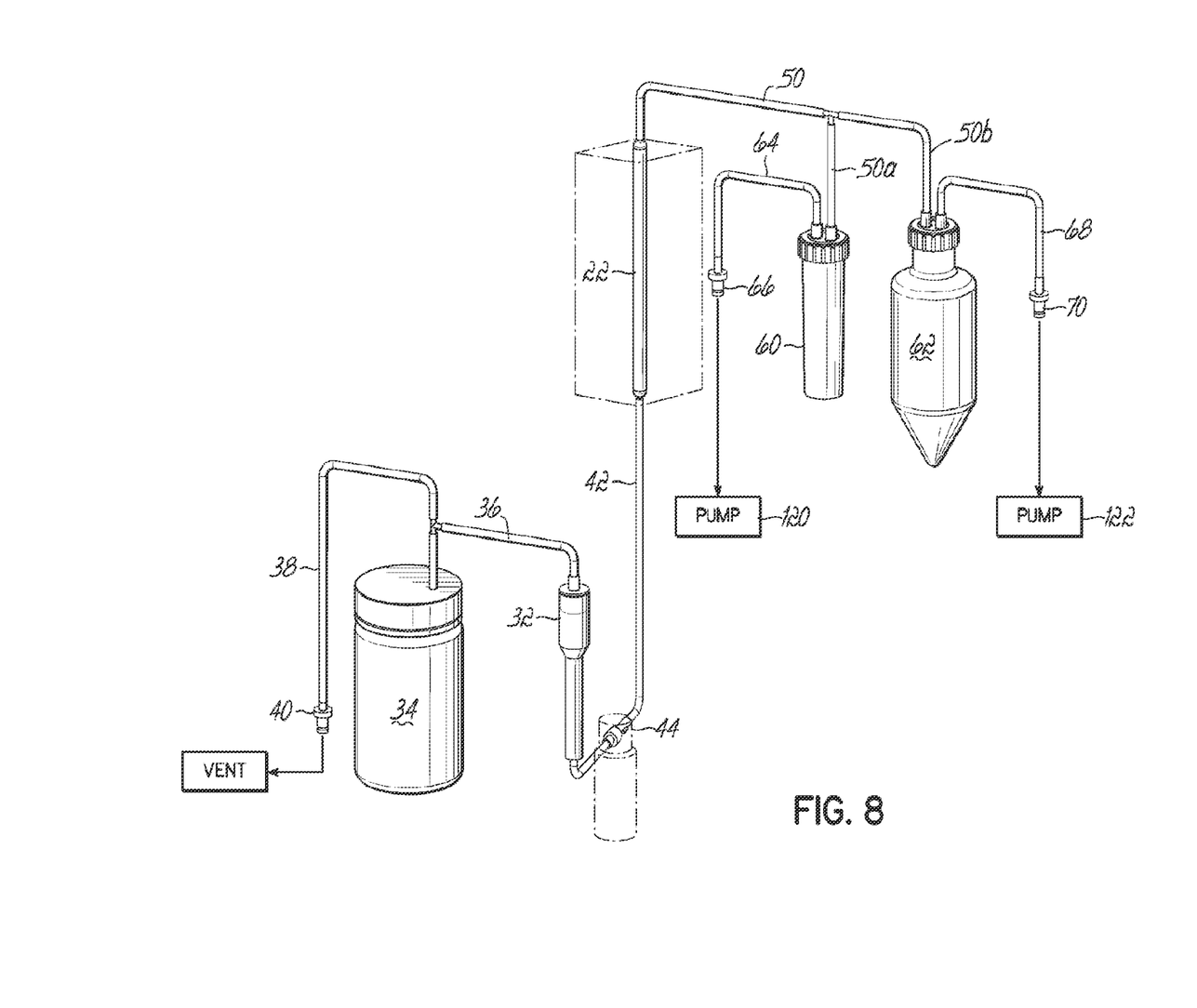
FIG. 8 is a perspective view of the disposable container and tubing system associated with the device of FIG. 1.

A biological cell sample container 32 is provided and receives a sample of biological cells, such as a blood sample, to be processed in the device 10. A buffer or suspension fluid container 34 receives a buffer fluid and is in fluid communication with the cell sample container 32 via an inlet conduit 36. A venting conduit 38 is also in fluid communication with the buffer fluid container 34 and leads to a fitting 40 and a vent (FIG. 8). An outlet conduit 42 of cell sample container 32 extends through a slot 44a in a pinch valve 44. The various conduits associated with the device 10 are preferably formed of a highly flexible material, such as silicone, so that they may be opened and closed to fluid flow using the illustrated pinch valves, including pinch valve 44, for reasons to be explained below. Conduit 42 leads to the inlet end 22a of the separator tube 22 as best shown in FIG. 2.

Still referring to FIGS. 1-3, a conduit 50 is in fluid communication with the outlet end 22b of the separator tube 22 and splits into respective conduits 50a and 50b. Conduit 50a extends through a pinch valve 52, while conduit 50b extends through pinch valve 54. Conduits 50a and 50b are respectively directed into a separated cell container 60 and a flushing fluid container 62. A pump conduit 64 communicates with the interior of the separated cell container 60 and leads to a positive displacement pump 120 (FIG. 8) via a fitting 66. Another pump conduit 68 leads to a fitting 70 and a second pump 122 (FIG. 8). Pump conduit 68 communicates with the interior of the flushing fluid container 62.

Turning more specifically to FIG. 2, the magnet 20 is mounted for vertical, linear movement along respective rails 80 (only one shown in FIG. 2) via linear motion elements 82 and mounting structure 84 affixed with the magnet 20. A screw drive receiving assembly 86 is coupled with a screw drive element 90 such that when the screw drive element 90 is rotated by a motor 92, the screw drive receiving assembly 86 and the attached mounting structure 84 and magnet 20 will move vertically along the screw drive element 90. In this illustrative embodiment, therefore, a motorized drive unit 96 is formed generally by elements 82, 84, 86, 89 and 82, Although not shown, the separator tube 22 may be suitably clipped or mounted at the top to the device 10 so that it remains stationary and stable relative to the magnet 20 and does not drop downwardly through the magnet 20.

Figure 7:
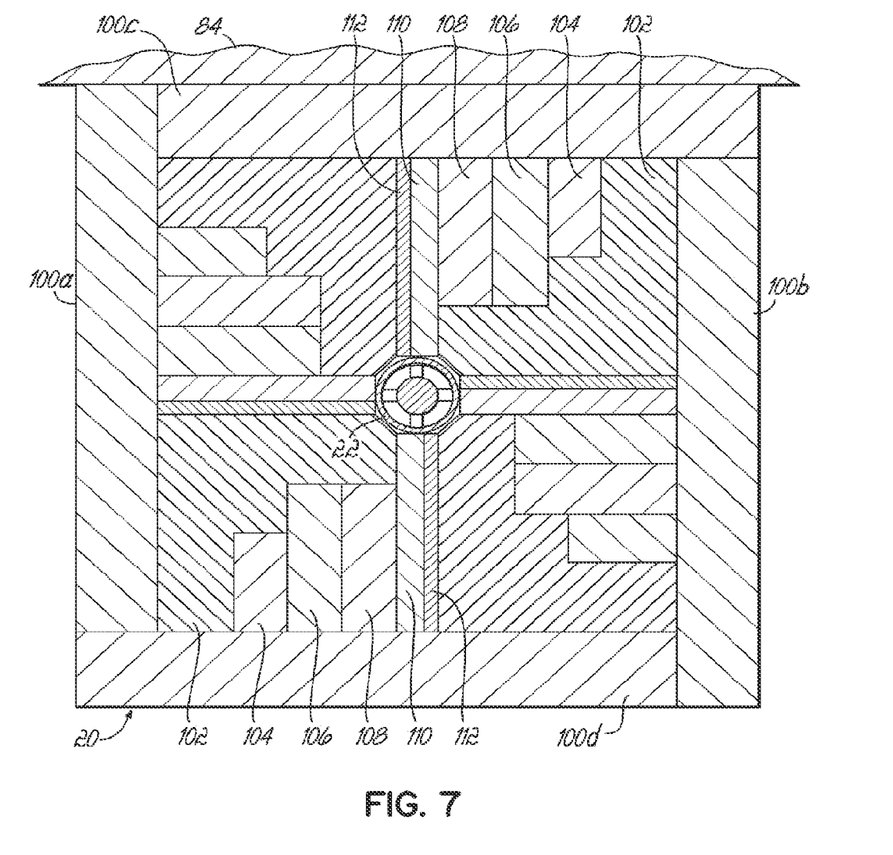
FIG. 7 is a cross sectional view of the magnet and separator tube taken in a plane perpendicular to the longitudinal axis thereof.

Referring now to FIGS. 4-7, the magnet 20 comprises an assembly of various components including four outer, nonmagnetic (e.g., aluminum) plates 100a, 100b, 100c, 100d that provide a casing for four magnet assemblies. Each magnet assembly, as best shown in FIG. 7 comprises an elongate element 102 having a stepped configuration in cross section and formed of a magnetic material, such as iron. Element 102 receives a series of permanent magnet plate elements 104, 106, 108, 110, 112. Upper and lower end caps 116, 118 are coupled with each assembly and are formed of nonmagnetic material, such as aluminum, to contain the magnetic field at opposite ends of the magnet 20.

OPERATION

The operation of the device 10 will now be described in connection with FIGS. 1, 2 and 8. A biological cell sample fluid is prepared and placed into the cell sample container 32. This sample may be a blood sample prepared in the manner described by the above-incorporated patent application. The size of the sample may, for example, be 5 ml. Pinch valves 44 and 52 are each in an open condition allowing fluid flow through conduits 42 and 50, 50a. Pinch valve 54 is closed to prevent fluid flow past the pinch valve 54 in conduit 50b. The positive displacement pump 120 is operated at a flow rate of, for example, 5 ml/min. to apply vacuum to the system, including to the interior of the separated cell container 60 via the pump conduit 64, conduits 50a, 50 leading to the interior annular flow channel of the separator tube 22 as well as conduit 42, sample cell container 32, conduit 36, and the buffer fluid container 34. This applied vacuum draws buffer fluid into the cell sample container 32. Approximately 30 ml of fluid is thereby collected in the separated cell container 60 by drawing the 5 ml sample and 25 ml of buffer fluid through the separator tube 22 and into the container 60. During this initial draw of fluid using the positive displacement pump 120, the magnetic cells are attracted and adhered to the interior wall of the separator tube 22 by the magnet 20 generally as discussed in the above-incorporated patent application. One difference between the magnet 20 and the previously disclosed magnet of the above-incorporated patent application is that magnet 20 develops a substantially uniform magnetic field along the length of the separator tube, as opposed to a magnetic field of gradually increasing magnitude.

After the initial draw of 30 ml fluid, pinch valves 44 and 52 are closed and the system at least temporarily shuts down. If the user desires to operate the device 10 in a flushing mode, the magnet 20 is moved downwardly by the motorized drive unit so as to completely expose the separator tube 22. This at least substantially entirely removes the magnetic field from the length of the separator tube 22, however, the cells are still adhered to each other and to the inside wall of the tube. Pinch valves 44 and 54 are then opened, while pinch valve 52 is closed. The high flow diaphragm pump 122 is then activated at a flow rate of, for example, 200 ml/min. to draw additional buffer fluid through the system and flush or wash the cells adhered to the interior of the separator tube 22 out of the separator tube 22 and into the flushing fluid container 62 via conduit 50b. It will be understood that if the user only has interest in collecting the nonmagnetic cells initially collected in the separated cell container 60, the user may choose not to perform the flushing step. The fluid and cells in the container 60/or and 62 may be further processed and analyzed as desired. These containers 60 and 62, as well as the other components, including the containers 32, 34, silicone tubing and separator tube 22 shown in FIG. 8 may comprise a disposable kit or system that is designed for one-time use with the device 10. Thus, to avoid contamination from process-to-process, a new disposable kit or system, such as shown in FIG. 8, may be utilized with the device 10 each time a sample cell separation is performed.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or any combinations depending on the needs and preferences of the user. However, the invention itself should only be defined by the appended claims.

What is claimed is:

1. A disposable kit for directing a fluid sample of biological cells through a separator device and collecting separated cells from the sample, the kit comprising:
   a sample receiving container including an inlet and an outlet, the inlet coupled with an inlet conduit for receiving a buffer fluid and the outlet coupled with an outlet conduit, the outlet conduit comprising a first section and a second section;
   a separator tube including an inlet end and an outlet end, the inlet end coupled with the outlet conduit from the sample receiving container, the separator tube having:
   a length defining a separation channel;
   a diameter adapted for operable communication with a magnet along the length of the separation channel;
   a space for receiving a flow of the buffer fluid and sample, and wherein a length of the second section of the outlet conduit from the sample receiving container is oriented along a path defined by the separator tube and adapted to allow displacement of the magnet from a separation position to an idle position while the flow of fluid is maintained;
   a separated cell container having an inlet port and a vacuum port,
   a separated cell conduit coupled for fluid communication between the outlet end of the separator tube and the inlet port of the separated cell container,
   a flushing fluid container having an inlet port and a vacuum port; and
   a flushing conduit coupled for fluid communication between the outlet end of the separator tube and the inlet port of the flushing fluid container.

2. The kit of claim 1, further comprising:
   a buffer fluid container coupled with the inlet conduit to the sample receiving container.

3. The kit of claim 1, wherein at least a portion of the outlet conduit from the sample receiving container comprises a flexible tubing for receipt within a first pinch valve.

4. The kit of claim 1, wherein at least a portion of the separated cell conduit comprises a flexible tubing for receipt within a second pinch valve.

5. The kit of claim 1, wherein at least a portion of the flushing conduit comprises a flexible tubing for receipt within a third pinch valve.

6. The kit of claim 1, further comprising a venting conduit connected for fluid communication with the flushing fluid container.

7. The kit of claim 1, further comprising a first pump conduit coupled with the vacuum port of the separated cell container, and a second pump conduit coupled with the vacuum port of the flushing fluid container.

* * * * *